United States Patent [19]

Cugola et al.

[11] Patent Number: 5,374,649

[45] Date of Patent: Dec. 20, 1994

[54] INDOLE DERIVATIVES AND PHARMACEUTICAL USE THEREOF

[75] Inventors: Alfredo Cugola; Giovanni Gaviraghi, both of Verona, Italy

[73] Assignee: Glaxo S.p.A., Verona, Italy

[21] Appl. No.: 47,430

[22] Filed: Apr. 15, 1993

[30] Foreign Application Priority Data

Apr. 16, 1992 [GB] United Kingdom ............... 9208492

[51] Int. Cl.$^5$ .................. C07D 209/18; A61K 31/405
[52] U.S. Cl. .................................... 514/719; 548/492
[58] Field of Search .......................... 548/492; 514/415

[56] References Cited

U.S. PATENT DOCUMENTS

| | | | |
|---|---|---|---|
| 3,010,971 | 11/1961 | Kaiser et al. | 260/319 |
| 4,960,786 | 10/1990 | Salituro et al. | 514/419 |
| 5,043,334 | 8/1991 | Bell et al. | 514/207 |
| 5,145,845 | 9/1992 | Johnson et al. | 514/80 |
| 5,284,862 | 2/1994 | Bigge et al. | 514/419 |

FOREIGN PATENT DOCUMENTS

| | | |
|---|---|---|
| 0396124 | 11/1990 | European Pat. Off. . |
| WO92/01670 | 2/1992 | WIPO . |
| WO92/16205 | 10/1992 | WIPO . |

OTHER PUBLICATIONS

Salituro et al., *J. Med. Chem.*, 1992, 35, 1791–1799.
Rowley et al., *Bioorganic & Medicinal Chemistry Letters*, 1992, 2(12), 1627–1630.
Salituro et al., *J. Med. Chem.*, 1990, 33, 2946–2948.
Gray et al., *J. Med. Chem.*, 1991, 34, 1283–1292.

*Primary Examiner*—David B. Springer
*Attorney, Agent, or Firm*—Bacon & Thomas

[57] ABSTRACT

The invention relates to compounds of formula I.

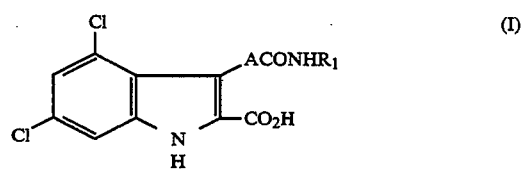

(I)

or a salt, or metabolically labile ester thereof wherein A represents an unsubstituted ethenyl, group in the trans configuration, $R_1$ represents a substituted phenyl group which are antagonists of excitatory amino acids, to processes for their preparation and to their use in medicine.

14 Claims, No Drawings

INDOLE DERIVATIVES AND PHARMACEUTICAL USE THEREOF

This invention relates to novel indole derivatives to processes for their preparation, to pharmaceutical compositions containing them and to their use in medicine. In particular it relates to indole derivatives which are potent and specific antagonists of excitatory amino acids.

U.S. Pat. No. 4,960,786 discloses that certain known 2-carboxylic indole derivatives are antagonists of excitatory amino acids. EP-A 0396124 also teaches that certain 2-carboxylic indole derivatives as being therapeutically effective in the treatment of CNS disorders resulting from neurotoxic damage or neurodegenerative diseases.

We have now found a novel group of 2-carboxyindole derivatives that have a highly potent and specific antagonist activity at the strychnine insensitive glycine binding site located on the NMDA receptor complex.

Accordingly the present invention provides a compound of formula (I).

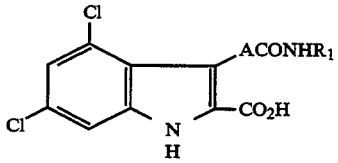

or a salt, or metabolically labile ester thereof wherein A represents an unsubstituted ethenyl group in the trans configuration; $R_1$ represents a substituted phenyl group.

For use in medicine the salts of the compounds of formula (I) will be physiologically acceptable thereof. Other salts however may be useful in the preparation of the compounds of formula (I) or physiologically acceptable salts thereof. Therefore unless otherwise stated references to salts includes both physiologically acceptable salts and non-physiologically acceptable salts of compounds of formula (I).

Suitable physiologically acceptable salts of compounds of the invention include base addition salts and where appropriate acid addition salts.

Suitable physiologically acceptable base addition salts of compounds of formula (I) include alkali metal or alkaline metal salts such as sodium, potassium, calcium, and magnesium, and ammonium salts formed with amino acids (e.g. lysine and arginine) and organic bases ( e.g. procaine, phenylbenzylamine, ethanolamine diethanolamine and N-methyl glucosamine).

It will be appreciated that the compound of formula (I) may be produced in vivo by metabolism of a suitable prodrug. Such prodrugs may be for example physiologically acceptable metabolically labile esters of compounds of the general formula (I). These may be formed by esterification, for example of any of the carboxylic acid groups in the parent compound of general formula (I) with where appropriate prior protection of any other reactive groups present in the molecule followed by deprotection if required. Examples of such metabolically labile esters include $C_{1-4}$alkyl esters e.g. methyl or ethyl esters, substituted or unsubstituted aminoalkyl esters (e.g. aminoethyl, 2-(N,N-diethylamino) ethyl, or 2-(4-morpholino)ethyl esters) or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-methoxy-1-methyl-ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxycarbonyloxyethyl) or 1-(4-tetrahydropyranylcarbonyloxyethyl.

Preferred metabolically labile esters of compounds of formula (I) include $C_{1-4}$alkyl esters more particular methyl or ethyl, aminoalkyl esters more particular 2-(4'-morpholino)ethyl, or acyloxyalkyl esters e.g. acetoxymethyl pivaloxymethyl, 1-cyclohexyloxycarbonyloxyethyl or 1-(4-tetrahydropyranyloxycarbonyloxy)ethyl.

The compounds of formula (I) and salts and metabolically labile esters thereof may from solyates e.g. hydrates and the invention includes such solyates.

The term substituted phenyl group refers to a phenyl group substituted by one or more groups selected from alkoxy, alkyl, amino, alkylamine, dialkylamino, fluoro, chloro, hydroxy, nitro, trifluoromethyl or $COR_2$, wherein $R_2$ is hydroxy or methoxy.

The term alkyl as used herein as a group or part of a group refers to a straight or branched chain alkyl group containing from 1 to 4 carbon atom.

A preferred class of compound of formula (I) are those wherein R is a phenyl substituted by one or two groups selected from fluorine trifluoromethyl, alkyl e.g. methyl or isopropyl, hydroxy, alkoxy e.g. methoxy or ethoxy or nitro Preferred compounds of the invention include
(E)-3-[2-(4-ethoxyphenylcarbamoyl)ethenyl)-4,6-dichloroindole-2-carboxylic acid;
(E)-3-[2-(2-hydroxy-5-nitrophenylcarbamoyl)ethenyl)-4,6-dichloroindole-2-carboxylic acid;
(E)-3-[2-(2-methyl-4-methoxyphenylcarbamoyl)ethenyl)-4,6-dichloroindole-2-carboxylic acid;
(E)-3-[2-(2-isopropylphenylcarbamoyl)ethenyl)-4,6-dichloroindole-2-carboxylic acid;
(E)-3-[2-(2,4-difluorophenylcarbamoyl)ethenyl)-4,6-dichloroindole-2-carboxylic acid;
(E)-3-[2-(3,4-dimethoxyphenylcarbamoyl)ethenyl)-4,6-dichloroindole-2-carboxylic acid;
and physiologically acceptable salts thereof e.g. sodium or potassium salts and metabolically labile esters thereof.

The compounds of formula (I) and or physiologically acceptable salts thereof are excitatory amino acid antagonists. More particularly they are potent antagonists at the strychnine insensitive glycine binding site associated with the NMDA receptor complex. As such they are potent antagonists of the NMDA receptor complex. Moreover the compounds of the invention exhibit an advantageous profile of activity including good bioavailibility. These compounds are therefore useful in the treatment or prevention of neurotoxic damage or neurodegenerative diseases. Thus the compounds are useful for the treatment of neurotoxic injury which follows cerebral stroke, thromboembolic stroke, hemorrhagic stroke, cerebral ischemia, cerebral vasospam, hypoglycemia, anaesia, hypoxia, anoxia, perinatal asphyxia cardiac arrest. The compounds are useful in the treatment of chronic neurodegenerative diseases such as; Huntingdon's disease, Alzheimer's senile dementia, amyotrophic lateral sclerosis. Glutaric Acidaemia type, multi-infarct dementia, status epilecticus, contusive injuries (e.g. spinal cord injury), viral infection induced neurodengeration, (e.g. AIDS, encephatopaties), Down syndrome, epilepsy, schizophrenia, depression, anxiety, pain, neurogenic bladder, irritative bladder disturbances, drug dependency, including withdrawal symptoms from alcohol, cocaine, opiates, nicotine, benzodiazepine.

The potent and selective action of the compounds of the invention at the strychnine- insensitive glycine binding site present on the NMDA receptor complex may be readily determined using conventional test procedures. Thus the ability to bind at the strychnine insensitive glycine binding site was determined using the procedure of Kishimoto H et al. J Neurochem 1981, 37 1015-1024. The selectivity of the action of compounds of the invention for the strychnine insensitive glycine site was confirmed in studies at other ionotropic known excitatory amino acid receptors. Thus compound of the invention were found to show little or no affinity for the kainic acid (kainate) receptor, a-amino-3-hydroxy-5-methyl-4-isoxazole-proprionic acid (AMPA) receptor or at the NMDA binding site.

Compounds of the invention have also been found to inhibit NMDA induced convulsions in mice using the procedure Chiamulera C et al. Psychopharmacology (1990) 102, 551–552.

The invention therefore provides for the use of a compound of formula (I) and or physiologically acceptable salt or metabolically labile ester thereof for use in therapy and in particular use as medicine for antagonising the effects of excitatory amino acids upon the NMDA receptor complex.

The invention also provides for the use of a compound of formula (I) and/or a physiologically acceptable salt or metabolically labile ester thereof for the manufacture of a medicament for antagonising the effects of excitatory amino acids upon the NMDA receptor complex.

According to a further aspect the invention also provides for a method for antagonising the effects of excitatory amino acids upon the NMDA receptor complex, comprising administering to a patient in need thereof an antagonistic amount of a compound of formula (I) and-/or a physiologically acceptable salt or metabolically labile ester thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated the route of administration and the age and the condition of the patient and will be ultimately at the discretion of the attendant physician. In general however doses employed for adult human treatment will typically be in the range of 2 to 800 mg per day, dependent upon the route of administration.

Thus for parenteral administration a daily dose will typically be in the range 20-100 mg preferably 60-80 mg per day. For oral administration a daily dose will typically be within the range 200-800 mg e.g. 400-600 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt or metabilcially labile ester thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant, or rectal administration. Parenteral administration is preferred.

Tablets and capsules for oral administration may contain conventional excipients such as binding agents, for example, syrup, accacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellant, such as dichlorodifluoromethane, tirchlorofluoromethane, dichloro-tetrafluoroethane, carbon dioxide or other suitable propellant, such as dichlorodifluoromethane, trichlorofluoromethane, dichloro-tetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in for example capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of formula (I) may be prepared from compound (II) in which $R_3$ is a carboxyl protecting group,

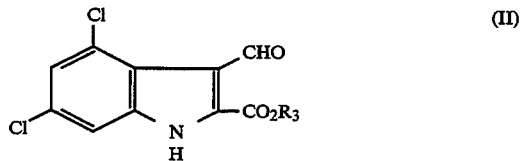

(II)

by reaction with an appropriate phosphorus ylide capable of converting the group CHO into the group ACONHR$_1$ wherein $R_1$ has the meanings defined above for formula (I) followed where necessary or desired by removal of the carboxyl protecting group.

Suitable carboxyl protecting groups include allyl, alkyl, trichloroalkyl, trialkylsilylalkyl or arymethyl groups such as benzyl, nitrobenzyl or trityl. In one embodiment of this process the reaction may be carried using a phosphorus ylide of formula (III)

(III)

wherein $R_4$ is an alkyl or phenyl group, and X and $R_1$ have the meanings defined above.

The reaction is carried out in aprotic solvent such as acetonitrile or an ether such as 1,4-dioxane and preferably with heating e.g. 40°–120°.

In the above reaction the carboxyl protecting group $R_3$ may be removed by conventional procedures known for removing such groups. Thus the group $R_3$, may be removed by hydrolysis using an alkali metal hydroxide e.g. lithium hydroxide in a solvent such as ethanol, followed where desired or necessary by that addition of a suitable acid e.g. hydrochloric acid to give the corresponding free carboxylic acid.

Physiologically acceptable salts of compounds of formula (I) may be prepared by treating the acid with the appropriate base e.g. alkali or alkaline earth metal hydroxide in an appropriate solvent such as an alkanol e.g. methanol.

Metabolically labile esters of compounds of formula (I) may be prepared by esterification of the carboxylic acid group or a salt thereof or by trans esterification using conventional procedures. Thus for example acyloxyalkyl esters may be prepared by reacting the free carboxylic acid or a salt thereof with the appropriate acyloxylalkyl halide in a suitable solvent such as dimethylformamide. For the esterification of the free carboxyl group this reaction is preferably carried out in the presence of a quaternary ammonium halide such as tetrabutylammonium chloride or benzyltriethylammonium chloride.

Aminoalkyl esters may be prepared by transesterification of a corresponding alkyl ester e.g. methyl or ethyl ester by reaction with the corresponding aminoalkanol at an elevated temperature e.g. 50°–150°.

Compounds of formula (II) wherein $R_3$ is a carboxyl protecting group, may be prepared by treating the corresponding indole (VIII).

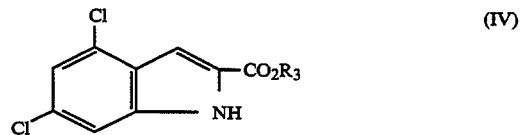

(IV)

wherein $R_3$ has the meanings defined above, with N-methylformanilide and phosphours oxychloride in a solvent such as 1,2-dichloroethane.

In the Intermediates and Examples unless otherwise stated:

Melting points (m.p.) were determined on a Gallenkamp m.p. apparatus and are uncorrected. All temperature refer to C.Infrared spectra were mesured on a FT-IR instrument. Proton Magnetic Resonance ($^1$H-NMR) spetra were recorded at 300 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). Colum chromathography was carrier out over silica gel (Merck A. G. Darmstaadt, Germany). The following abbrevietions are used in text: EA=ethyl acetate, CH=cyclohexane, DCM=dichlormethane, DBU=1,8 diazabicyclo[5.4.0]undec-7-ene. DMF=NM-dimethylformamide, THF=tetrahydrofuran, LiOH.H$_2$ lithium hydroxide monohydrate. Tlc refers to a thin layer chromatography on silica plates. Solution were dried over anhydrous sodium sulphate.

Intermediate 1

Ethyl 4,6-dichloroindole-2-carboxylate

To a solution of ethyl pyruvate (2.05 ml), in absolute ethanol (38 ml), concentrated sulphuric acid (0.5 ml) was added slowly under vigorous stirring. The resulting mixture was stirred at 23 for 10 minutes, then 3,5-dichlorophenylhydrazine hydrochloride (4 g) was added portionwise. The mixture was heated to reflux for 4 hours, cooled to 23°, poured into cold water (500 ml) and extracted with diethyl ether (3×300 ml). The organic layers were separated and dried. The solvent was evaporated under reduced pressure to give the 2-(3,5-dichlorophenylhydrazone)propionic acid ethyl ester as yellow solid (5 g; tlc DCM, Rf=0.79, 0.47) in E and Z isomers mixture. The solid was added to polyphosphoric acid (20 g) under stirring and the mixture was heated at 45° for 20 minutes to give a brown product which was crystallized by 95% ethanol (300 ml) to obtain the title compound as a yellow-brown solid (3.3 g; m.p.180°; Tlc DCM, Rf=0.54). IR(CDCl$_3$) Vmax(cm$^{-1}$)3440(NH), 1772–1709(C=O).

Intermediate 2

Ethyl 3-formyl-4,6-dichloroindole-2-carboxylate

A solution of N-methyl formanilide (5.19 g) and phosporous oxychloride (5.53 g) was stirred at 23° for 15 minutes. 1,2- Dichloroethane (60 ml) and intermediate 1 (6 g) were added and the resulting suspension was stirred at 80° for 6 hours. The reaction mixture was poured into a 50% aqueous solution of sodium acetate (300 ml) to give, by filtration, the title compound as a yellow solid (4.1 g; tlc EA/CH:4/6, Rf=0.4).

EXAMPLE 1A (E)Ethyl 3-[2-(4-trifluoromethylpbenylcarbamoyl)ethenyl]-4,6-dichloroindole-2-carboxylate To a stirred-suspension of 4-(trifluoromethyl)phenyl-carbamoyl-methyltriphenylphosphonium chloride (0.99 g) in acetonitrile (10 ml) at 0° under nitrogen, DBU (0.3 g) was added. Stirring was continued at 0° for 25 minutes then intermediate 2 (0.56 g) was added and the mixture was refluxed for 8 h. After dilution with dichloromethane (20 ml), the formed precipitate was collected by filtration giving the title compound (0.6 g;) tlc EA/CH:4/6 Rf=0.49 ) as a white solid.

IR(Nujol) Vmax(cm$^{-1}$) 3310(NH), 1676(C=O), 1632, 1612(C=C).

EXAMPLE 1B (E)Ethyl 3-[2-(2-isopropylphenyl)carbamoylethenyl]-4,6-dichloroindole-2-carboxylate To a stirred suspension of (2-isopropylphenyl)carbamoyl-phenylmethyltriphenylphosphonium chloride (0.83 g) in acetonitrile (10 ml) at 0° under nitrogen, DBU was added. Stirring was continued at 0° for 20 minutes then intermediate 2 (0.5 g) was added and the mixture refluxed for 4 h. After dilution with dichloromethane (20 ml) the formed precipitate was collected by filtration giving the title compound (340 mg; tlc EA/CH:4/6 Rf=0.53) as a white solid.

IR(Nujol)Vmax(cm$^{-1}$)3304(NH), 1676, 1659(C=O).

EXAMPLE 1C (E)Ethyl 3-[2-(2-nitrophenylcarbamoyl)ethenyl]-4,6-dichloroindole-2-carboxylate To a stirred suspension of (2-nitrophenyl)carbamoyl-methyl-triphenylphosphonium chloride (0.75 g) in acetonitrile (10 ml) at 0° under nitrogen, DBU (238 mg) was added. Stirring was continued at 0° for 20 minutes then intermediate 2 (0.45 g) was added and the mixture refluxed for 4 h. After dilution with dichloromethane (20 ml) the formed precipitate was collected by filtration giving the title compound (420 mg; tlc EA/CH:4/6 Rf=0.55) as a yellow solid.

IR(Nujol) Vmax(cm$^{-1}$) 3348–3308(NH), 1672(C=O), 1607–1590(C=C), 1556–1346(NO$_2$).

EXAMPLE 1D (E) Ethyl 3-[2-(2-methyl-4-methoxyphenylaminocarbonyl)ethenyl]-4,6-dichloroindole-2-carboxylate To a suspension of (2-methyl-4-methoxyphenyl)aminocarbonylmethyl-triphenylphosphonium chloride (0.998 g) in acetonitrile (15 ml) at 0° under nitrogen, DBU (0.32 g) was added. Stirring was continued at 0° for 25 minutes then intermediate 2 (0.6 g) was added and the mixture was refluxed for 3 hours. After dilution with dichloromethane (20 ml), the formed precipitate was collected by filtration giving the title compound (0.57 g; tlc EA/CH:4/6 Rf=0.34) as an off-white solid.

IR(Nujol)V$_{max}$(cm$^{-1}$)3302–3246(NH), 1678–1659(C=O), 1624(C=C).

EXAMPLE 1E (E) Ethyl 3-[2-(2-hydroxyphenylaminocarbonyl)ethenyl]-4,6-dichloroindole-2-carboxylate To a suspension of (2-hydroxyphenyl)aminocarbonylmethyl-triphenylphosphonium chloride (0.94 g) in acetonitrile (15 ml) at 0° C. under nitrogen, DBU (0.32 g) was added. Stirring was continued at 0° for 25 minutes then intermediate 2 (0.6 g) was added and the mixture was stirred for 24 h at room temperature. The suspension was evaporated to dryness and the residue purified by flash-chromatography(EA/CH:3/7 then 4/6) giving the title compound (0.37 g; tlc EA/CH:4/6 Rf=0.39) as a beige solid.

IR(Nujol)V$_{max}$(cm$^{-1}$)3317–3290(NH), 1678–1655(C=O), 1618(C=C).

EXAMPLE 1F (E) Ethyl3-[2-(3,4-dimethoxyphenylaminocarbonyl)ethenyl]-4,6-dichloroindole-2-carboxylate To a suspension of (3,4-dimethoxyphenyl)aminocarbonylmethyl-triphenylphosphonium chloride (0.69 g) in acetonitrile (10 ml) at 0° under nitrogen, DBU (0.21 g) was added. Stirring was continued at 0° for 25 minutes then intermediate 2 (0.4 g) was added and the mixture was stirred overnight at room temperature then refluxed for 3 hours. After dilution with dichloromethane (20 ml), the formed precipitate was collected by filtration giving the title compound (0.457 g; tlc EA/CH:4/6 Rf=0.20) as a yellow solid.

IR(Nujol)V$_{max}$(cm$^{-1}$)3317–3254(NH), 1678(C=O), 1620–1600(C=C).

EXAMPLE 1G (E) Ethyl 3-[2-(4-ethoxyphenylaminocarbonyl)ethenyl]-4,6-dichloroindole-2-carboxylate To a suspension of (4-ethoxyphenyl)aminocarbonyl-methyl-triphenylphosphonium chloride (0.67 g) in acetonitrile (10 ml) at 0° under nitrogen, DBU (0.21 g) was added. Stirring was continued at 0° for 25 minutes then intermediate 2 (0.6 g) was added and the mixture was refluxed for 28 hours. After dilution with dichloromethane (20 ml), the formed precipitate was collected by filtration giving the title compound ) (0.265 g; tlc EA/CH:4/6 Rf=0.41) as a light yellow solid.

IR(Nujol)V$_{max}$(cm$^{-1}$)3321–3260(NH), 1676(C=O), 1622(C=C).

EXAMPLE 1H (E) Ethyl 3-[2-(2,4-difluorophenylaminocarbonyl)ethenyl]-4,6-dichloroindole-2-carboxylate To a suspension of (2,4-difluorophenyl)aminocarbonylmethyl-triphenylphosphonium chloride (0.655 g) in acetonitrile (10 ml) at 0° under nitrogen, DBU (0.21 g) was added. Stirring was continued at 0° C. for 25 minutes then intermediate 2 (0.4 g) was added and the mixture was refluxed for 26 hours. After dilution with dichloromethane (20 ml), the formed precipitate was collected by filtration giving the title compound (0 42 g; tlc EA/CH:4/6 Rf=0.54) as a light yellow solid.

IR(Nujol)$V_{max}$(cm$^{-1}$)3298(NH), 1678–1661(C=O), 1624(C=C).

EXAMPLE 1I (E) Ethyl 3-[2-(2-fluoro-5-nitrophenylaminocarbonyl)ethenyl]-4,6-dichloroindole-2-carboxylate To a suspension of (2-fluoro-4-nitrophenyl)aminocarbonylmethyl-triphenylphosphonium chloride (0.52 g) in acetonitrile (10 ml) at 0° under nitrogen, DBU (0.16 g) was added. Stirring was continued at 0° for 25 minutes then intermediate 2 (0.3 g) was added and the mixture was refluxed for 18 hours. After dilution with dichloromethane (20 ml), the formed precipitate was collected by filtration giving the title compound (0.34 g; tlc EA/CH:4/6 Rf=0.41 ) as a beige solid.

IR(Nujol)n$_{max}$(cm$^{-1}$)3300(NH), 1680–1666(C=O), 1545–1377(NO$_2$)

EXAMPLE 2A (E)3-[2-Trifluoromethylphenylcarbamoyl)ethenyl]-4,6-dichloroindole-2-carboxylic acid Lithium hydroixde (208 g) was added to a solution of Example 1A (585 g) in ethanol (5ml) at 23°. The reaction mixture was stirred at 50° for 6 hr, the solvent evaporated and the residue dissolved in water (10 ml). The aqueous layer was acidified with 1N hydrochloride acid until a white solid precipitated which was collected and dried to give the title compound was obtained as a light brown solid (520 mg).

IR(nujol) Vmax(cm$^{-1}$) 3430–3000(NH,OH), 1700–1678(C=O), 1636–1614(C=C). $^1$H-NMR (DMSO) 14–13.5(s), 12.55(s), 10.54(s), 8.37(d), 7.91(d), 7.67(d), 7.48(d), 7.30(d), 6.86(d).

Using the same general procedure the following compounds were prepared.

EXAMPLE 2B (E)3-[2-(2-Isopropylphenylcarbamoyl)ethenyl]-4,6-dichloroindole-2-carboxylic acid dilithium salt Starting from Example 1B (317 mg), the title compound was obtained as a light brown solid (288 mg).

IR(nujol) Vmax(cm$^{-1}$) 3661(NH,OH), 1610(C=O). $^1$H-NMR (DMSO) 12.1(s), 9.39(s), 8.57(d), 7.57(s), 7.38–7.28(m), 7.28–7.10(m), 3.25(m), 1.15(d).

EXAMPLE 2C (E)3-[2-(2-Nitrophenylcarbamoyl)ethenyl]-4,6-dichloroindole-2-carboxylic acid Starting from Example 1C (440 mg), the title compound was obtained as a yellow solid (290 mg).

IR(nujol) Vmax(cm$^{-1}$) 3234(NH,OH), 1684–1636(-C=O), 1639(C=C). $^1$H-NMR (DMSO) 12.2(s), 10.51(s), 8.59(d), 7.95(dd), 7.81(dd), 7.69(m), 7.48(d), 7.38–7.28(m), 7.20(d).

EXAMPLE 2D (E) 3-[2-(2-Methyl-4-methoxyphenylaminocarbonyl)ethenyl]-4,6-dichloroindole-2-carboxylic acid Starting from Example 1D (0.54 g), the title compound was obtained as a yellow solid (0.39 g).

IR(Nujol)V$_{max}$(cm$^{-1}$)3279(NH,OH), 1703–1661(-C=O), 1630(C=C). $^1$H-NMR(DMSO) 12.41(s), 9.39(s), 8.26(d), 7.48(d), 7.36(d), 7.27(d), 6.90(d), 6.80(d), 6.75(dd), 3.73(s), 2.19(s).

EXAMPLE 2E (E) 3-[2-(2-Hydroxyphenylaminocarbonyl)ethenyl]-4,6-dichloroindole-2-carboxylic acid Starting from Example 1E (0.34 g), the title compound was obtained as a yellow-brown solid (0.33 g).

IR(Nujol)V$_{max}$(cm$^{-1}$)3150(NH,OH), 1736–1656(-C=O), 1630(C=C). $^1$H-NMR(DMSO) 12.56(s), 9.97(s), 9.76(s), 8.24(s), 7.8(d), 7.49(d), 7.30(d), 6.96(d), 6.96(td), 6.88(dd), 6.79(td).

EXAMPLE 2F (E) 3-[2-(3,4-Dimethoxyphenylaminocarbonyl)ethenyl]-4,6-dichloroindole-2-carboxylic acid Starting from example 1F (0.41 g), the title compound was obtained as a light yellow solid (0.38 g).

IR(Nujol)V$_{max}$(cm$^{-1}$)3420–2381 (NH), 1690–1680(-C=O), 1620–1607(C=C). 1H-NMR(DMSO) 13.8–13.6(s), 12.53(s), 10.08(s), 8.23(d), 7.47(m), 7.29(d), 7.20(dd), 6.89(d), 6.74(d), 3.37(s), 3.70(s).

EXAMPLE 2G (E) 3-[2(4-Ethoxyphenylaminocarbonyl)ethenyl]-4,6-dichloroindole-2-carboxylic acid Starting from example 1G (0.25 g), the title compound was obtained as a light yellow solid (0.22 g).

IR(Nujol)n$_{max}$(cm$^{-1}$)3248(NH,OH), 1663(C=O), 1632–1610(C=C). 1H-NMR(DMSO) 13.7(s), 12.50(s), 10.04(s), 8.22(d), 7.61(d), 7.47(d), 7.29(d), 6.86(d), 6.74(d), 3.97(q), 1.29(t).

EXAMPLE 2H (E) 3-[2-(2,4-Difluorophenylaminocarbonyl)ethenyl]-4,6-dichloroindole-2-carboxylic acid Starting from example 1H (0.41 g), the title compound was obtained as a light yellow solid (0.37 g).

IR(Nujol)n$_{max}$(cm$^{-1}$)3431–3233(NH,OH), 1707–1678(C=O), 1612(C=C). 1H-NMR(DMSO) 14.0–13.6(s), 12.54(s), 9.99(s), 8.29(d), 7.97(m), 7.48(d), 7.30(m), 7.29(d), 7.07(m), 6.90(d).

Pharmacy Examples

| A. Capsules/Tablets | |
|---|---|
| Active ingredient | 200.0 mg |
| Starch 1500 | 32.5 mg |

| A. Capsules/Tablets | |
| --- | --- |
| Microcrystalline Cellulose | 60.0 mg |
| Croscarmellose Sodium | 6.0 mg |
| Magnesium Stearate | 1.5 mg |

The active ingredient is blended with the other excipients. The blend can be used to fill gelatine capsules or compressed to form tablets using appropriate punches. The tablets can be coated using conventional technqiues and coatings.

| B. Tablet | |
| --- | --- |
| Active ingredient | 200.0 mg |
| Lactose | 100.0 mg |
| Microcrystalline Cellulose | 28.5 mg |
| Povidone | 25.0 mg |
| Croscarmellose Sodium | 6.0 mg |
| Magnesium Stearate | 1.5 mg |

The active ingredient is blended with lactose, microcrystalline cellulose and part of the croscarmellose sodium. The blend is granulated with povidone after dispersing in a suitable solvent (i.e. water). The granule, after drying and comminution is blended with the remaining excipients. The blend can be compressed using appropriate punches and the tablets coated using conventional techniques and coatings.

| C. Injection Formulation | |
| --- | --- |
| Active ingredient | 0.1–7.00 mg/ml |
| Sodium phosphate | 1.0–50.00 mg/ml |
| NaOH qs desidered pH (range 3-10) | |
| water for injection qs to | 1 ml |

The formulation may be packed in glass (ampoules) with a rubber stopper (vials, syringes) and a plastic/metal overseal (vials only).

| D. Dry Powder for constitution with a suitable vehicle | |
| --- | --- |
| Active ingredient: | 0.1–100.00 mg |
| Mannitol qs to | 0.02–5.00 mg | packed in glass vials or syringes, with a rubber stopper and (vials only) a plastic metal overseal.

| E. Inhalation Cartridges | |
| --- | --- |
| | mg/cartridge |
| Active ingredient (micronised) | 5.00 |
| Lactose to | 25.00 |

The active ingredient is micronised in a fluid energy mill to a fine particle size range prior to blending with normal tabletting grade lactose in a high energy mixer. The powder blend is filled into a proper unit dose container as blister or capsule for use in a suitable inhalation or insufflation device.

The affinity of the compound of the invention for strychnine insensitvie glycine binding site was determined using the procedure of Kishimoto H. et al J. Neurochem 1981, 37, 1015-1024. The pKi values obtained with respresentative compounds of the invention are given in the following table.

| Example No. | pKi |
| --- | --- |
| 2e | 8.4 |
| 2f | 8.1 |
| 2g | 8.3 |
| 2h | 8.3 |
| 2i | 8.0 |

The ability of compounds of the invention to inhibit NMDA included convulsions in the mouse was determined using the procedure of Chiamulera C et al. Psychopharmacology 1990, 102, 551–552. In this test the ability of the compound to inhibit the generalized seizures induced by an intracerebroventricular injection of NMDA in mice was examined at a number of dose levels. From these results the dose required to protect 50% of the animals from the convulsive action of the NMDA was calculated. This expressed as mg/kg is referred to as the $ED_{50}$ value.

Representative results obtained for compounds of the invention when given by intravenous administration are given in the following table.

| Ex No. | $ED_{50}$ iv |
| --- | --- |
| 2f | 0.3 |
| 2g | 0.1 |
| 2h | 0.3 |

We claim:
1. A compound of formula (I)

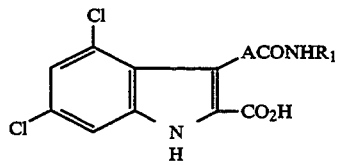

or a physiologically acceptable salt or a metabolically labile ester thereof, wherein:
A represents an unsubstituted ethenyl group, in the trans configuration;
$R_1$ represents a phenyl group substituted by one or more groups selected from the group consisting of $C_{1-4}$alkyl, $C_{1-4}$alkoxy, amino, $C_{1-4}$alkylamino, di-$C_{1-4}$alkylamino, fluoro, chloro, hydroxy, nitro, trifluoromethyl, or $COR_2$, wherein $R_2$ is hydroxy or methoxy.

2. A compound as claimed in claim 1 wherein the $R_1$ is a phenyl group substituted by one or two groups selected from fluorine, trifluromethyl, methyl, isopropyl, hydroxy, methoxy, ethoxy or nitro.

3. The compounds:
(E)-3-[2-(4-ethoxyphenylcarbamoyl)ethenyl)-4,6-dichloroindole-2-carboxylic acid;
(E)-3-[2-(2-hydroxy-5-nitrophenylcarbamoyl)ethenyl)-4,6-dichloroindole-2-carboxylic acid;
(E)-3-[2-(2-methyl-4-methoxyphenylcarbamoyl)ethenyl)-4,6- dichloroindole-2-carboxylic acid;
(E)-3-[2-(2-isopropylphenylcarbamoyl)ethenyl)-4,6-dichloroindole-2-carboxylic acid;
(E)-3-[2-(2,4-difluorophenylcarbamoyl)ethenyl)-4,6-dichloroindole-2-carboxylic acid;
(E)-3-[2-(3,4-dimethoxyphenylcarbamoyl)ethenyl)-4,6-dichloroindole-2-carboxylic acid; and physiologically acceptable salts and metabolically labile esters thereof.

4. A metabolically labile ester of a compound as claimed in any of claims 1 to 3.

5. A compound as claimed in claim 1, which is (E)3-[2-(trifluoromethylphenylcarbamoyl)ethenyl]-4,6-dichloroindole-2-carboxylic acid.

6. A compound as claimed in claim 1, which is (E)3-[2-(2-isopropylphenylcarbamoyl)ethenyl]-4,6-dichloroindole-2-carboxylic acid, dilithium salt.

7. A compound as claimed in claim 1, which is (E)3-[2-(2-nitrophenylcarbamoyl)ethenyl]-4,6-dichloroindole-2-carboxylic acid.

8. A compound as claimed in claim 1, which is (E)3-[2-(2-methyl-4-methoxyphenylaminocarbonyl)ethenyl]-4,6-dichloroindole-2-carboxylic acid.

9. A compound as claimed in claim 1, which is (E)3-[2-(2-hydroxyphenylaminocarbonyl)ethenyl]-4,6-dichloroindole-2-carboxylic acid.

10. A compound as claimed in claim 1, which is (E)3-[2-(3,4-dimethoxyphenylaminocarbonyl)ethenyl]-4,6-dichloroindole-2-carboxylic acid.

11. A compound as claimed in claim 1, which is (E)3-[2-(4-ethoxyphenylaminocarbonyl)ethenyl]-4,6-dichloroindole-2-carboxylic acid.

12. A compound as claimed in claim 1, which is (E)-3-[2-(2,4-difluorophenylaminocarbonyl)ethenyl]-4,6-dichloroindole-2-carboxylic acid.

13. A pharmaceutical composition comprising a compound in any of claims 1 to 4 in admixture with one or more physiologically acceptable carriers or excipients.

14. A method of treatment of a mammal including man for conditions where antagonising the effects of excitatory amino acids on the NMDA receptor complex is of therapeutic benefit comprising administration of an effective amount of a compound as claimed in any of claims 1 to 4.

* * * * *